(12) United States Patent
Ford

(10) Patent No.: US 6,270,721 B1
(45) Date of Patent: Aug. 7, 2001

(54) SEPARATOR DEVICE FOR ARTICLE STERILIZATION

(76) Inventor: Christopher W. Ford, 86 Labbe La., Leonard, MI (US) 48367-2950

( * ) Notice: Subject to any disclaimer, the term of this patent is extended or adjusted under 35 U.S.C. 154(b) by 418 days.

(21) Appl. No.: 08/728,787

(22) Filed: Oct. 10, 1996

(51) Int. Cl.[7] ....................................... A61L 2/20
(52) U.S. Cl. ......................... 422/28; 422/297; 422/300
(58) Field of Search ................................ 422/297, 300, 422/28; 211/180, 59.4, 70.1

(56) References Cited

U.S. PATENT DOCUMENTS

| 2,467,331 | * | 4/1949 | Mock | 422/300 X |
| 2,512,747 | * | 6/1950 | Lewis | 422/300 X |
| 3,838,679 | * | 10/1974 | Welch | 211/70.1 X |
| 4,150,629 | * | 4/1979 | Santi | |

* cited by examiner

Primary Examiner—Elizabeth McKane
(74) Attorney, Agent, or Firm—Harness, Dickey & Pierce, P.L.C.

(57) ABSTRACT

A separator device to separate a plurality of articles in a sterilization chamber has a proximal end, a distal end, and a body portion therebetween. The body portion has a thickness with a plurality of openings therein through which a sterilizing medium circulates. The body portion is interposed between and maintains separation between layers of articles located within the sterilization chamber. The separation maintained between the layers facilitates circulation of the sterilizing medium between the layers and to each of the plurality of articles being sterilized.

18 Claims, 3 Drawing Sheets

SEPARATOR DEVICE FOR ARTICLE STERILIZATION

BACKGROUND OF THE INVENTION

1. Technical Field

This invention relates to article sterilization and, more particularly, to a separator device to increase the loading capacity of a sterilization chamber in which articles are sterilized via a sterilizing medium.

2. Discussion

It is well known to sterilize articles such as medical and dental instruments in order to kill all microbes associated with the instruments. Common methods of sterilization include autoclaving, i.e. steam sterilization, chemical-vapor sterilization, and dry heat sterilization. Typically, articles requiring steam or chemical-vapor sterilization are packaged in permeable containers such as pouches, bags, wraps, wrapped trays, or cassettes prior to placement within a sterilization chamber. A typical sterilization chamber includes a plurality of trays upon which the containers or the individual articles themselves are placed for exposure to a particular sterilizing medium. Unfortunately, in order to assure that the sterilizing medium reaches and completely sterilizes all of the articles in the sterilization chamber, the containers should not be stacked higher than two layers thick on any given tray. This limitation assures that the sterilization medium properly flows between each of the layers to properly sterilize all the articles. A problem with layering the containers is that the majority of the sterilization chamber's volume is not effectively utilized. This presents problems in high volume applications where sterilization capacity is limited and sterilization of large quantities of articles is required. In the high volume applications, the containers are often stacked higher than two layers such that the weight of the additional layers prevents the sterilization medium from effectively flowing between each of the layers. This inhibits the sterilizing medium from moving between each of the layers and allows the microbes to survive and be transmitted upon reuse of the articles. In previous applications, additional sterilization chambers are required to accommodate the high volumes of articles. However, this only increases costs without improving the efficiency at which a sterilization chamber's fixed volume is utilized.

Likewise, in dry heat or forced-air dry heat sterilizers, the containers or individual articles must be placed to optimize air circulation throughout the interior volume of a sterilization chamber. Preferably, each of the containers or individual articles are separated by a distance of at least one-half inch. Proper air circulation ensures that the articles are uniformly and thoroughly heated to kill all microbes. As discussed above, the containers should not be stacked beyond two layers high. This leads to overcrowding which prevents instruments located within inner layers from reaching a proper temperature required for effective sterilization and/or requires lengthening the sterilization cycle to attain the proper temperature.

Previous attempts to overcome problems include adding additional trays within a fixed volume sterilization chamber, adding vertical separators within the chamber to vertically align the containers, or using expensive cassettes that provide spacing between the articles. However, none of these solutions provides for maximum use of a sterilization chambers fixed volume.

It is therefore desirable to provide a separator device to increase the loading capacity of a sterilization chamber that does not require multiple trays, metal vertical separators, or cassettes to completely sterilize articles.

More particularly, it is desirable to provide a separator device that is relatively simple and inexpensive to manufacture, reusable, and provides sufficient separation between multiple layers of the articles. These features facilitate circulation of a sterilizing medium between the multiple layers and throughout the sterilization chamber.

SUMMARY OF THE INVENTION

In accordance with the teachings of the present invention, a separator device to separate a plurality of articles in a sterilizing chamber is disclosed. The separator device includes a proximal end and a distal end. A body portion is between the ends and includes a thickness with a plurality of openings that enable circulation of a sterilization medium. The length of the body portion is placed between layers of plurality of articles to maintain separation between the respective layers. The separation maintained between the layers facilitates circulation of the sterilizing medium throughout the body portion and between the layers to sterilize the plurality of articles.

In accordance with a preferred embodiment, the body portion is folded in order to form predetermined lengths between the proximal and distal ends.

In accordance with another embodiment, the body portion is formed from a woven mesh material to facilitate circulation of the sterilization medium.

BRIEF DESCRIPTION OF THE DRAWINGS

The various advantages of the present invention will become apparent to those skilled in the art after reading the following specifications and by reference to the drawings in which:

FIGS. 5a–5c illustrate a method of using the separator device for sterilizing a plurality of articles within a sterilization chamber in accordance with the teachings of the present invention.

DETAILED DESCRIPTION OF THE PREFERRED EMBODIMENTS

The following description of the preferred embodiments is merely exemplary in nature and is in no way intended to limit the invention or its application or uses.

The present invention is particularly concerned with a device to increase the loading capacity of a sterilization chamber. This is accomplished by maintaining separation between multiple layers of articles which are sterilized via a circulating sterilizing medium. The separator device of the present invention is simple to operate, reusable, and inexpensive to manufacture. While the present invention will be described in accordance with the use of a flexible woven metallic mesh material, the use of other suitably porous materials that can withstand the heated and pressurized environment within a sterilization chamber are within the scope of the present invention.

Figure 1:
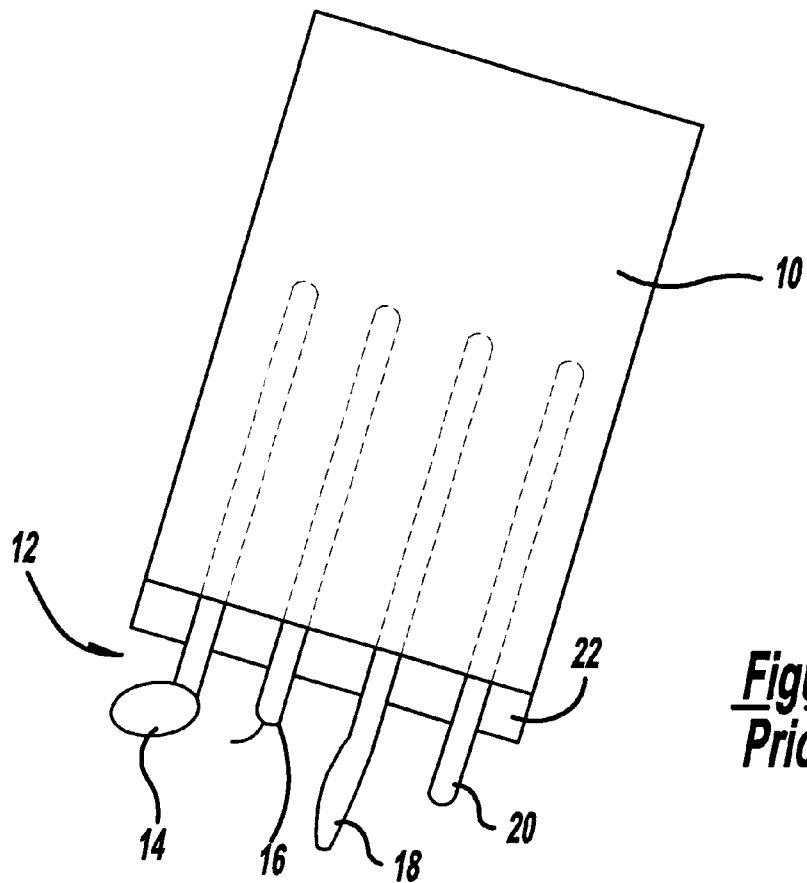
FIG. 1 is a plan view of a typical permeable container in which a plurality of articles are placed which require sterilization.

Referring to FIG. 1, a typical container 10 in which articles 12 commonly employed in the medical and dental fields are inserted prior to sterilization in a sterilization chamber is shown. The articles 12 include, but are not limited to, a dental mirror 14, an explorer instrument 16, a scalpel instrument 18 and a miscellaneous hand instrument 20. Other types of articles which require sterilization are also within the scope of the present invention. During the sterilization process, the articles 12 are fully inserted within the container 10. The container 10 is sealed via an adhesive lip portion 22. The container 10 is a pouch type container made from a permeable paper material. The sterilizing medium, such as steam, penetrates the paper material in order to contact and sterilize the articles 12. Typically, this type of container has a width ranging from 2 to 4 inches and a length ranging from 6 to 12 inches. By way of example, the container 10 is a Peelvue Autoclave/ Chemiclave Pouch available from Clive Craig having a width of 3.25 inches and a length of 12 inches.

Figure 2:
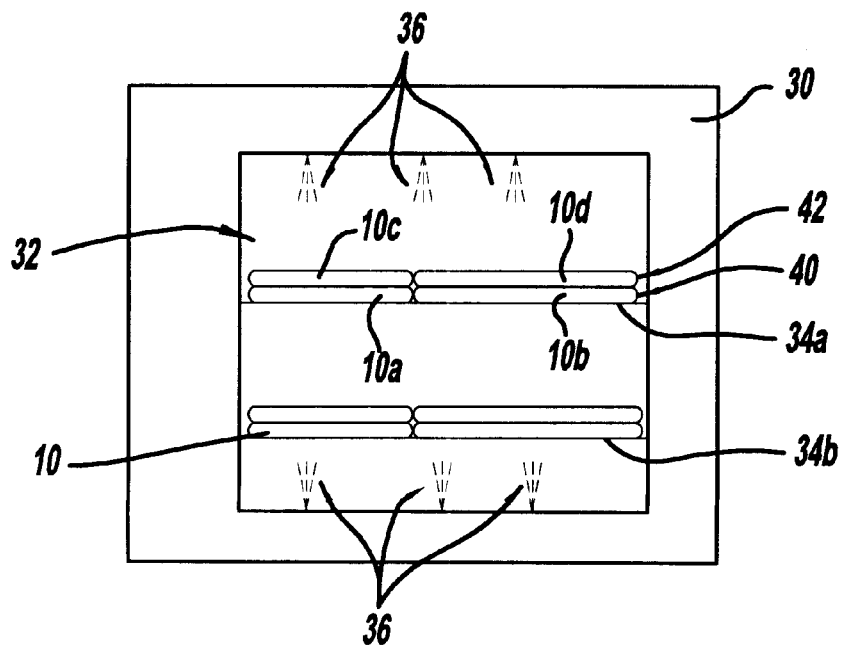
FIG. 2 is a schematic illustration of a prior sterilization chamber with a plurality of trays each having two layers of the permeable containers.

Turning to FIG. 2, a sterilization chamber 30 having an interior volume 32 is schematically illustrated. The chamber 30 includes tray members 34a and 34b each located at different levels within the interior volume 32. A plurality of containers 10, each containing articles 12, are stacked upon the trays 34a and 34b. A sterilizing medium 36 such as, but not limited to, steam supplied at a predetermined temperature and pressure circulates throughout the interior volume 32 to sterilize the articles 12. With specific reference to tray 34a, a first layer 40 of containers 10a and 10b are loaded directly upon the tray 34a. A second layer 42 of containers 10c and 10d are disposed on top of the first layer 40. Unfortunately, in order to assure proper circulation of the sterilizing medium 36 and sterilization of the articles 12 within the chamber 30, the containers 10 should not be stacked more than two layers high on either of the trays 34a and 34b. This is because the added weight of additional layers causes the layers to compact which inhibits the sterilizing medium from flowing between the layers. As will be apparent, depending upon the specific dimensions of the containers 10, the layers 40 and 42 may contain additional or less containers 10 for a particular sized sterilization chamber. Another problem with such a layering limitation is that the interior volume 32 of the chamber 30 is not fully or effectively utilized, i.e. large spaces exist between the trays 34a and 34b where additional containers 10 could be located for sterilization. Unfortunately, additional layers of containers 10 are often placed within these unused spaces causing overcrowding and preventing the articles 12 located within inner layers of the containers 10 from being properly sterilized.

Figure 3:
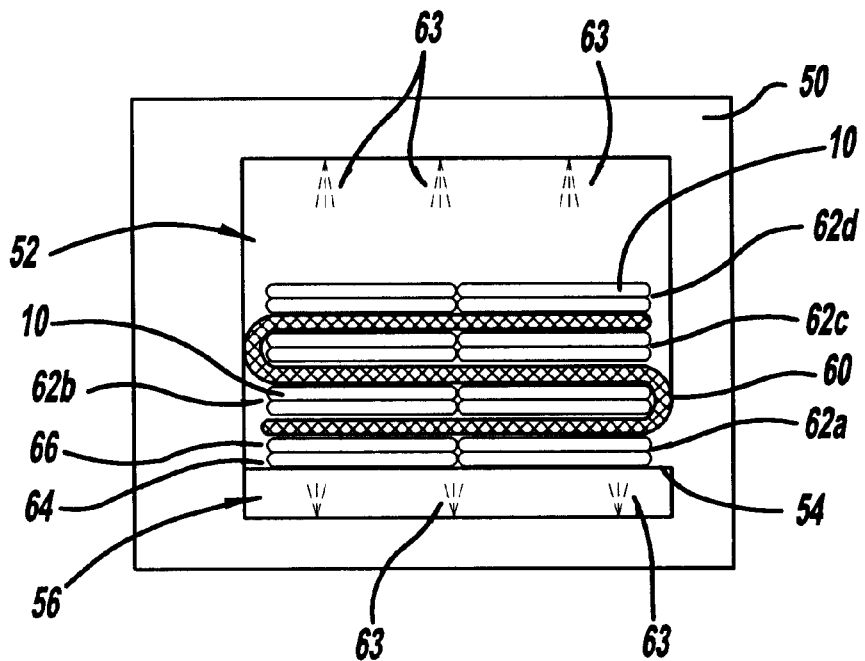
FIG. 3 is a schematic illustration of a sterilization chamber with a single tray upon which a plurality of layers of the permeable containers are stacked with a separator device interposed therebetween in accordance with the teachings of the present invention.

Turning to FIG. 3, a schematic illustration of a sterilization chamber 50 having an interior volume 52 equal to that of sterilization chamber 30 is shown. A single tray 54 is located in a lower portion 56 of the interior volume 52 to receive articles. In order to efficiently utilize the interior volume 52 and increase the loading capacity of the chamber 50, a separator device 60 is interposed between layers of containers 10. As illustrated, various pairs of layers 62a, 62b, 62c, and 62d of containers 10 are stacked upon the tray 54 to a desired height within the interior volume 52. A first layer 64 of containers 10a and 10b are loaded directly upon the tray 54, and a second layer 66 of containers 10c and 10d are disposed directly on top of the first layer 64.

The separator device 60 is placed between and maintains separation between the pairs of layers 62a–62d. As with the sterilizing chamber 30, a sterilizing medium 63 such as, but not limited to, pressurized steam is circulated throughout the interior volume 52 to sterilize each of the articles 12 located within each of the containers 10. The separator device 60 is formed from a flexible porous material which enables sterilizing medium 63 to flow freely between each of the pairs of layers 62a–62d as well as between each of the individual layers. The medium 63 flow assures that all of the articles 12 within the chamber 50 are properly sterilized. As will be apparent to one skilled in the art, the device 60 can be interposed between each of the individual layers of containers 10, as opposed to being disposed between the pairs of layers 62a–62d, in order to increase the circulation of the sterilizing medium 63. Also, the device 60 can be used to maintain separation between individual articles loaded in layers within the chamber 60.

Figure 4:
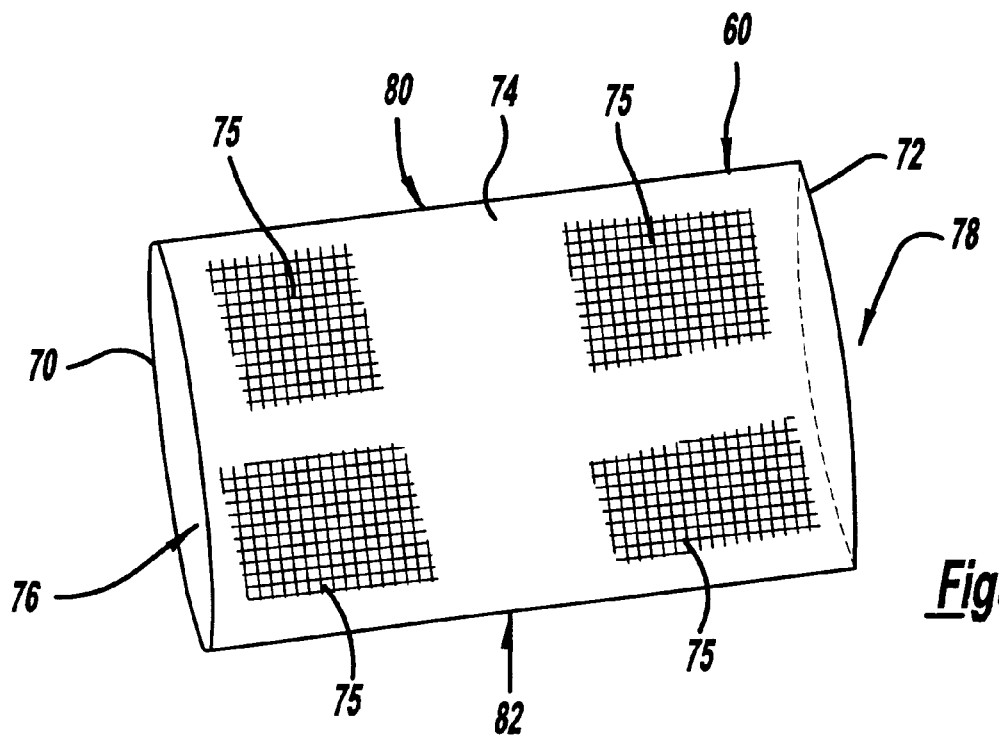
FIG. 4 is a perspective view of the separator device in accordance with the teachings of the present invention.

With reference to FIG. 4, the separator device 60 is formed from a length of woven mesh material having a proximal end 70, a distal end 72 and a body portion 74. Preferably, the device 60 is made from woven stainless steel thread or wire such that the body portion 74 is porous. Numerous openings 75 in the body portion 74 enable flow of the sterilizing medium 63 between each of the pairs of layers 62a–62d of containers 10. The body portion 74 is formed as a continuous loop with the proximal end 70 to define a first opening 76 and the distal end 72 to define a second opening 78. Edges 80 and 82, formed by crimping the main body portion 74, extend between the proximal end 70 and the distal end 72 such that the device 60 is substantially planar when positioned between the layers of containers 10. This reduces the volume occupied by the device 60. The woven construction provides the device 60 with a sufficient thickness to maintain desired spacing between the pairs of layers 62a–62d of containers 10. Also, the construction provides an avenue for flow of the sterilizing medium 63. The thickness of the body portion 74 is controlled primarily by the gage of the wire used to form the device 60. Alternatively, rather than being formed as a continuous loop, the body portion 74 may be formed from a single planar length of woven material. This would reduce the body thickness by approximately one half. Also, the width of the device 60 is controlled simply by weaving additional material to increase its width for a desired application. The device 60 is especially useful due to its ability to be customized to any given length for a particular application. The device 60 is simply disposed between and folded around edges of the various layers of containers 10. Another advantage of the present invention is that the device 60 is reusable and resistant to the heated environment within the sterilization chamber 50.

Figure 5A:
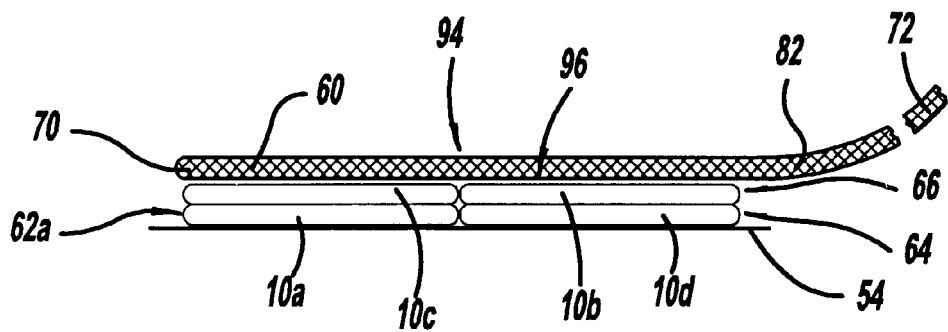
Figure 5C:
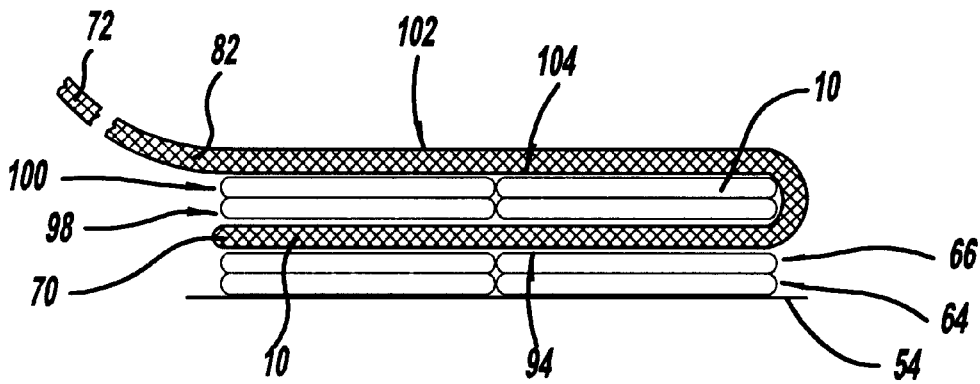
Figure 5C:
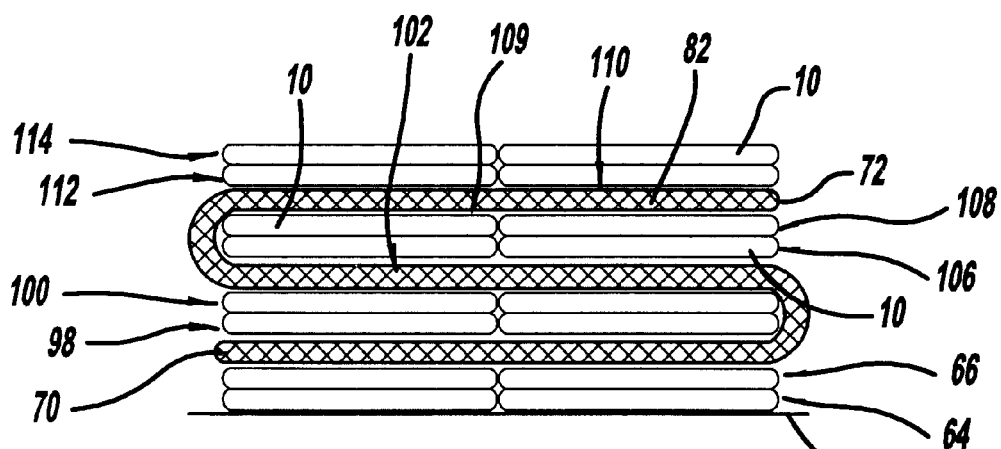

Turning to FIGS. 5a–5c, the method of using the separator device 60 to sterilize a plurality of articles 12 located within numerous containers 10 within the sterilization chamber 50 in FIG. 3 is shown. As will be apparent, the method is also applicable to sterilize articles individually loaded in layers within the sterilizing chamber 50.

In operation, the first and second layers 64 and 66 of containers 10a–10d are loaded upon the tray 54. A first length 94 of the separator device 60, beginning at the proximal end 70, is disposed lengthwise across a top surface 96 of the second layer 66 of containers 10c and 10d. The first length 94 is substantially planar and has a width between edges 80 and 82 that extends completely across the top surface 96. As shown in FIG. 5b, a third layer 98 and a fourth layer 100 of containers 10 are loaded across the first length 94 of the separator device 60. The first length 94 maintains separation between the second layer 66 and the third layer 98 of containers 10. The first length 94 provides an avenue for flow of the sterilizing medium 63 to sterilize the articles 12 contained within each of the containers 10. Next, the separator device 60 is folded around the third and fourth layers 98 and 100. A second length 102 is disposed across a top surface 104 of the fourth layer 100 of the containers 10. As illustrated, the separator device 60 is flexible so as to conform to the thicknesses of the various layers of articles being sterilized. Again, the second length 102 has a width between edges 80 and 82 that extends across the top surface 104.

With reference to FIG. 5c, fifth and sixth layers 106 and 108 of containers 10 are loaded across the second length 102 of the separator device 60. As illustrated, the second length 102 maintains separation between the fourth and fifth layers 100 and 106 of containers 10. The second length 102 provides another avenue for flow of the sterilizing medium 63. Thereafter, the separator device 60 is folded around the fifth and sixth layers 106 and 108 and a third length 110 of the device 60, ending at the distal end 72, is disposed across a top surface 109 of the sixth layer 108. The third length 110 has a width between edges 80 and 82 that extends across the top surface 109. Lastly, seventh and eighth layers 112 and 114 of containers 10 are loaded upon the third length 110. The third length 110 maintains separation between the sixth and seventh layers 108 and 112 of containers 10. The third length 110 provides an avenue for additional flow of the sterilizing medium 63. As will be apparent to one skilled in the art, depending upon the overall length of the separator device 60, additional layers of containers 10 may be placed within the sterilization chamber 50 to any desired height without lessening the effectiveness at which the sterilizing medium 63 flows between the layers to sterilize the articles 12. Alternatively, the first length 94, second length 102, and third length 110 of the separator device 60 may be formed as individual pieces of woven material that are individually placed between layers of containers 10.

When compared to prior sterilization methods, the use of the separator device 60 increases the loading capacity of a sterilization chamber without requiring costly retrofits while assuring proper sterilization of all the articles contained in multiple stacked layers.

The foregoing discloses and describes merely exemplary embodiments of the present invention. One skilled in the art will readily recognize from such discussion, and from the accompanying drawings and claims, that various changes, modifications and variations can be made therein without departing from the spirit and scope of the present invention as defined by the following claims.

What is claimed is:

1. A sterilizing separator device, comprising:
    a woven mesh material adapted to receive a sterilizing medium, said woven mesh material having a proximal end and a distal end; and
    a body portion between the proximal and distal ends, the body portion having a desired thickness with a plurality of openings therein through which said sterilizing medium circulates, the body portion being flexible and having a continuous length such that the body portion is randomly folded in a serpentine pattern so that the body portion is interposed between layers of articles to maintain separation between the layers of articles, and said flexible body conforming to the thickness of the various layers of articles as said body is folded, and the sterilizing medium circulates through the openings and sterilizes the articles.

2. The separator device of claim 1, wherein the body portion is folded to form predetermined lengths between the proximal and distal ends, each of the lengths being interposed between the layers of the articles.

3. The separator device of claim 2, wherein the body portion is a continuous loop with the proximal end defining a first opening and the distal end defining a second opening.

4. The separator device of claim 1, wherein the woven mesh material is a flexible metallic material.

5. A system for sterilizing a plurality of articles, comprising:
    a sterilization chamber having an interior volume in which the plurality of articles are loaded;
    a sterilizing medium circulating throughout the interior volume of the sterilization chamber to sterilize the plurality of articles; and
    separator means, said separator means being flexible and continuous and randomly folding so that the separator means is placed between layers of the plurality of articles, said flexible separator conforming to the thickness of the various layers of articles as it is folded, and maintaining separation between the layers such that the sterilizing medium freely circulates between the layers and sterilizes the plurality of articles.

6. The system of claim 5, wherein the separator means includes at least one length of woven mesh material including:
    a proximal end and a distal end; and
    a body portion between the ends, the body portion having a desired thickness with a plurality of openings therein through which a sterilization medium circulates, the body portion having a length that is interposed between layers of articles for maintaining separation between the layers such that the sterilizing medium circulates through the openings and sterilizes the articles.

7. The system of claim 6, wherein the body portion is folded to form predetermined lengths between the proximal and distal ends, each of the lengths are interposed between the layers of the plurality of articles.

8. The system of claim 7, wherein the woven mesh material is a flexible metallic material.

9. The system of claim 7, wherein the body portion is a continuous loop with the proximal end defining a first opening and the distal end defining a second opening.

10. The system of claim 5, wherein the sterilization chamber includes a tray member located in a lower portion of the interior volume for receiving the layers of the plurality of articles with the separator means interposed therebetween.

11. The system of claim 10, wherein the separator means includes at least one length of woven mesh material including:
    a proximal end and a distal end; and
    a body portion between the ends, the body portion having a desired thickness with a plurality of openings therein through which a sterilization medium circulates, the body portion having a length that is interposed between layers of articles to maintain separation between the layers such that the sterilizing medium circulates through the openings and sterilizes the articles.

12. The system of claim 11, wherein the body portion is folded to form predetermined lengths between the proximal and distal ends, each of the lengths are interposed between the layers of the plurality of articles.

13. The system of claim 12, wherein the woven mesh material is a flexible metallic material.

14. The system of claim 13, wherein the body portion is a continuous loop with the proximal end defining a first opening and the distal end defining a second opening.

15. A method of sterilizing a plurality of articles in a sterilization chamber having an interior volume in which a sterilizing medium circulates for sterilizing the plurality of articles, comprising the steps of:
   (a) loading first and second layers of the plurality articles within a lower section of the sterilization chamber; and
   (b) disposing a first length of a separator device across a top surface of the second layer of articles;
   (c) loading third and fourth layers of the plurality of articles across the first length of the separator device such that the separator maintains a predetermined distance between the second and third layers of the plurality of articles and said third and fourth layer of articles resting on the first length of the separator device such that it is sandwiched between the second layer of articles and the third layer of articles, thereby allowing circulation of the sterilizing medium between the layers for sterilization of the plurality of articles;
   (d) folding a second length of the separator device across a top surface of the fourth layer of articles where as the separator is flexible and continuous and said separator conforming to the thickness of the layers of articles as it is folded across the articles.

16. The method of claim 15 further comprising the steps of:
   (d) disposing a second length of the separator device across a top surface of the fourth layer of articles;
   (e) loading fifth and sixth layers of the plurality of articles across the second length of the separator device such that the separator device maintains a predetermined distance between the fourth and fifth layers of the plurality of articles.

17. The method of claim 16 wherein step (d) includes folding the separator device to form the second length.

18. The method of claim 15 wherein the separator device is formed from a flexible woven mesh material.

* * * * *